(12) United States Patent  
Locsin

(10) Patent No.: US 8,989,873 B2
(45) Date of Patent: Mar. 24, 2015

(54) INTRAVASCULAR MEDICAL DEVICE WITH ADVANCABLE ELECTRODE

(75) Inventor: Brent L. Locsin, San Francisco, CA (US)

(73) Assignee: Medtronic, Inc., Minneapolis, MN (US)

( * ) Notice: Subject to any disclaimer, the term of this patent is extended or adjusted under 35 U.S.C. 154(b) by 218 days.

(21) Appl. No.: 13/187,169

(22) Filed: Jul. 20, 2011

(65) Prior Publication Data

US 2013/0023975 A1 Jan. 24, 2013

(51) Int. Cl.
  *A61N 1/00* (2006.01)
  *A61N 1/05* (2006.01)
  *A61N 1/362* (2006.01)

(52) U.S. Cl.
  CPC ............. *A61N 1/0563* (2013.01); *A61N 1/362* (2013.01)
  USPC .............................. 607/122; 607/36; 607/116

(58) Field of Classification Search
  USPC ........ 607/36, 116, 122–123; 128/898; 606/41
  See application file for complete search history.

(56) References Cited

U.S. PATENT DOCUMENTS

| | | | |
|---|---|---|---|
| 5,170,802 A | 12/1992 | Mehra | |
| 6,070,104 A | 5/2000 | Hine et al. | |
| 6,445,953 B1 | 9/2002 | Bulkes et al. | |
| 6,971,394 B2 * | 12/2005 | Sliwa et al. | 128/898 |
| 7,082,336 B2 * | 7/2006 | Ransbury et al. | 607/126 |
| 7,236,821 B2 | 6/2007 | Cates et al. | |
| 7,627,376 B2 | 12/2009 | Dennis et al. | |
| 7,824,403 B2 * | 11/2010 | Vaska et al. | 606/41 |
| 8,357,153 B2 * | 1/2013 | Habib | 606/41 |
| 2003/0158584 A1 | 8/2003 | Cates et al. | |
| 2006/0178617 A1 * | 8/2006 | Adams et al. | 604/65 |
| 2007/0265673 A1 | 11/2007 | Ransbury et al. | |
| 2008/0147168 A1 | 6/2008 | Ransbury et al. | |
| 2008/0167702 A1 | 7/2008 | Ransbury et al. | |
| 2009/0276025 A1 * | 11/2009 | Burnes et al. | 607/126 |
| 2010/0137936 A1 * | 6/2010 | Dennis et al. | 607/33 |
| 2011/0071585 A1 | 3/2011 | Ransbury et al. | |

* cited by examiner

Primary Examiner — Catherine Voorhees
(74) Attorney, Agent, or Firm — Carol F. Barry

(57) ABSTRACT

Implantable medical devices and methods use an intravascular implantable medical device having an elongated housing module to contain one or more circuitry components. An opening is defined through the elongated housing module. A lead, including at least one electrode, is coupled towards the distal end of the elongated housing module and at least a portion of the at least one electrode is in a stowed position within the opening defined through the elongated housing module during implant of the implantable medical device. The at least one electrode is advanceable from the stowed position to a location distal of the distal end of the elongated housing module.

21 Claims, 10 Drawing Sheets

INTRAVASCULAR MEDICAL DEVICE WITH ADVANCABLE ELECTRODE

The disclosure herein relates to implantable medical devices, such as intravascular medical devices.

Medical devices related to managing, treating and providing therapy for cardiac conditions have changed and improved dramatically since their inception. Cardiac pacing, as an example, originally required an external pulse generator that itself required external power. While providing life sustaining therapy, patients were tethered to the power source and of course, power failures could prove problematic. Portable, battery powered external pulse generators were developed and provided the patient with the ability to be ambulatory; however, the pulse generator had to be carried by the patient. Furthermore, pacing leads were exposed through the patient's tissue and extreme care had to be exercised to minimize the risk of infection or inadvertent withdrawal.

Subsequently, fully implantable, battery powered pulse generators were provided in a hermetically sealed housing. This housing was rather large and was typically implanted in the abdomen of the patient, with leads extending to the heart. The size of such a device often made it rather uncomfortable and the implantation procedure was relatively invasive.

As technology improved, implantable medical devices (IMDs) have become continuously smaller, while offering increased longevity, reliability and many more features and therapies. Epicardial leads that were attached to an external wall of the heart were replaced with endocardial leads that are implanted transvenously, thus becoming minimally invasive. With these smaller devices, the housing was no longer placed in the abdomen but instead could be implanted subcutaneously or sub-muscularly, often in the pectoral region. For example, a "pocket" may be formed underneath the skin or muscle sufficiently large to receive the housing of the IMD. The exposed or proximal ends of the leads are then connected to the housing and the incision is closed. While now routine, this is still a surgical procedure that requires skill and the appropriate medical facilities.

In general, patients are comfortable with these implanted devices and have a full range of motion, without interference or hindrance. Some patients feel the housing in the "pocket;" which may be physically and/or psychologically uncomfortable. Physically, some patients may press against the housing during certain physical activities making the housing noticeable. Even if not a hindrance or painful, simply "feeling" the presence of the device may remind the patient that they have a medical implant and/or medical condition and this alone may be troubling to that patient. Some patients develop a habit of pressing against the pocket and hence against the IMD and often rotating or twisting the IMD. Typically, IMDs that have one or more leads will have any excess lead length coiled under (or around) the housing of the IMD. Thus, frequent patient manipulation may cause portions of the lead(s) to twist or rub, potentially damaging the lead body or pulling the lead out of contact with the targeted tissue.

As the size and capability of IMDs has greatly improved, use of these devices has naturally expanded. This results in greater knowledge and acceptance among the patient population as well as within the medical community. As a result, caregivers are using IMDs with more frequency and for new and diverse purposes. For example, pacemakers are used in patients with various bradyarrhythmias. In such a patient, the heart's intrinsic pacing function fails or is deficient and the IMD provides electrical stimulation to maintain the proper heart rhythm. Such therapy is well known. Recently, the medical community has been using pacing technology in patient's whose heart rhythm is actually normal. Heart failure patients often have normal rhythm and conduction; however, this disease causes the heart to enlarge. As a result, the left and right ventricles are unsynchronized when they contract even though the depolarization waveform triggering such a contraction was "timed" properly. Using cardiac resynchronization therapy (CRT), the left and right ventricles are paced, leading to a mechanical "resynchronization" of the left and right ventricular contractions. This not only leads to better immediate hemodynamic performance, but the heart itself often remodels itself (reducing in size) leading to an improvement in the disease state.

Not only are new therapies and treatments developing, implantable devices are now being used to collect sensor data for a variety of purposes. For example, implantable loop recorders (ILRs) are implanted subcutaneously and record cardiac data, unobtrusively, for extended periods of time. This allows robust medical data to be collected that, as a practical matter, may be otherwise unattainable.

As indicated above, the leads of IMDs (e.g., the length of such leads) may cause one or more difficulties. For example, implanting long lead wires involves a long procedure time, as well as increased risk of infection. Further, conventional lead wires travel all the way from the shoulder region (e.g., pocket) to the heart. With the heart constrained by the chest cavity which is in constant periodic motion, the continued cyclic displacement of the lead wires may lead to fatigue risk of the wires thereof.

SUMMARY

The disclosure herein relates to intravascular medical devices (e.g., a modular device; such as, a pacing module or capsule and associated leads, such as relatively short leads) that, for example, may be implanted in a vascular structure (e.g., coronary vein). For example, the module or capsule (e.g., containing all the electronic circuitry and battery power components needed for operation) may be implanted (e.g., passively fixated) in a proximal region of a vein. One or more leads (e.g., relatively short leads as compared to leads used to connect a pacing device in the shoulder region to the heart) may connect one or more electrodes to the module or capsule. The one or more electrodes may be more distally implanted in the vein (e.g., further distally along the tapered vein). In one or more embodiments, the module may include a thru-hole in which at least a portion of one or more of the electrodes may be housed (e.g., a stowed positioned), for example, during delivery of the module to the proximal region of the vein. Further, in one or more embodiments, the electrode may be advanced to the more distal implant region of the vein (e.g., using a pusher device to move the electrode from its stowed position).

One exemplary intravascular implantable medical device may include an elongated housing module extending between a proximal end and a distal end to contain one or more circuitry components (e.g., components for use in providing cardiac therapy or monitoring cardiac activity). An opening may be defined through the elongated housing module from the proximal end to the distal end. Further, the device may include a lead extending between a proximal end and a distal end (e.g., the proximal end of the lead may be coupled towards the distal end of the elongated housing module). The lead may include at least one electrode located in proximity to the distal end of the lead. At least a portion of the at least one electrode may be in a stowed position within the opening defined through the elongated housing module during implant of the implantable medical device. The at least one electrode may be advanceable from the stowed position to a location distal of the distal end of the elongated housing module.

An exemplary method (e.g., of implanting a device, providing therapy, etc.) may include advancing an implantable medical device to a primary intravascular site. For example, the implantable medical device may include an elongated housing module extending between a proximal end and a distal end to contain one or more circuitry components (e.g., for use in providing cardiac therapy or for monitoring physiological parameters of a patient). An opening may be defined through the elongated housing module from the proximal end to the distal end. Further, a lead extends between a proximal end and a distal end, wherein the proximal end of the lead is coupled towards the distal end of the elongated housing module. The lead may include at least one electrode located in proximity to the distal end of the lead, wherein at least a portion of the at least one electrode is in a stowed position within the opening defined through the elongated housing module as the implantable medical device is advanced to the primary intravascular site. The method further includes advancing the at least one electrode from the stowed position to another intravascular site distal of the distal end of the elongated housing module.

One or more embodiments of the exemplary devices and/or methods may include one or more of the following features: the elongated housing module may extend between the proximal end and the distal end along an axis and the opening defined through the elongated housing module may be centered along the axis or may be offset from the axis; the at least one electrode may include an electrode at the distal end of the lead and may be passively fixated at the distal end of the lead within vascular structure; passively fixating the electrode at the distal end of the lead within vascular structure may include lodging two opposing surface regions of the electrode within the vascular structure; the at least one electrode may include an outer surface configured for contact with the vessel wall of vascular structure and include an outer diameter in the range of 0.1 mm to 5 mm such that passively fixating the at least one electrode within vascular structure uses an interference fit between the outer surface and the vessel wall; two or more leads may be provided and each lead may include at least one electrode located in proximity to the distal end of the lead (e.g., wherein at least a portion of the at least one electrode of each lead may be in a stowed position within the opening defined through the elongated housing module and wherein the at least one electrode of each lead may be advanced from the stowed position to separate intravascular sites distal of the distal end of the elongated housing module); the elongated housing module may be passively fixated within vascular structure; the elongated housing module may include an outer surface configured for contact with the vessel wall of vascular structure and may include an outer diameter in the range of 4 mm to 15 mm such that passively fixating the elongated housing module within vascular structure uses an interference fit between the outer surface and the vessel wall; the lead may include a lead wire coupling the at least one electrode to the one or more circuitry components contained within the elongated housing module and wherein at least a portion of the lead wire may be in a stowed position within the opening defined through the elongated housing module during implant of the implantable medical device (e.g., the lead wire with the at least one electrode may be advanced from the stowed position to the intravascular site distal of the distal end of the elongated housing module); and the lead may include a lead wire coupling the at least one electrode to the one or more circuitry components contained within the elongated housing module and at least a portion of the lead wire may be in a stowed position within a containment section in the elongated housing module during implant of the implantable medical device (e.g., the lead wire with the at least one electrode may be advanced from the stowed position to the intravascular site distal of the distal end of the elongated housing module).

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1:
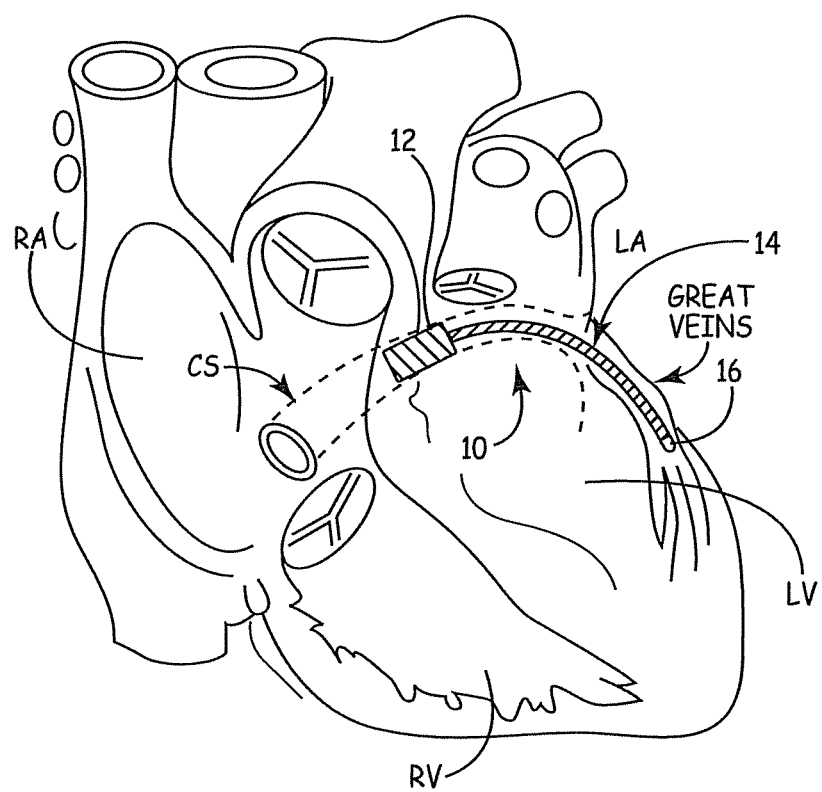
FIG. 1 is an illustration of an exemplary embodiment of an intravascular medical device (IVMD) implanted in a coronary vein of a patient's cardiac system.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary methods and devices shall be described with reference to FIGS. 1-12. It will be apparent to one skilled in the art that elements or processes from one embodiment may be used in combination with elements or processes of the other embodiments, and that the possible embodiments of such methods, devices, and systems using combinations of features set forth herein is not limited to the specific embodiments shown in the figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/ or sizes, or types of elements, may be advantageous over others.

Figure 2:
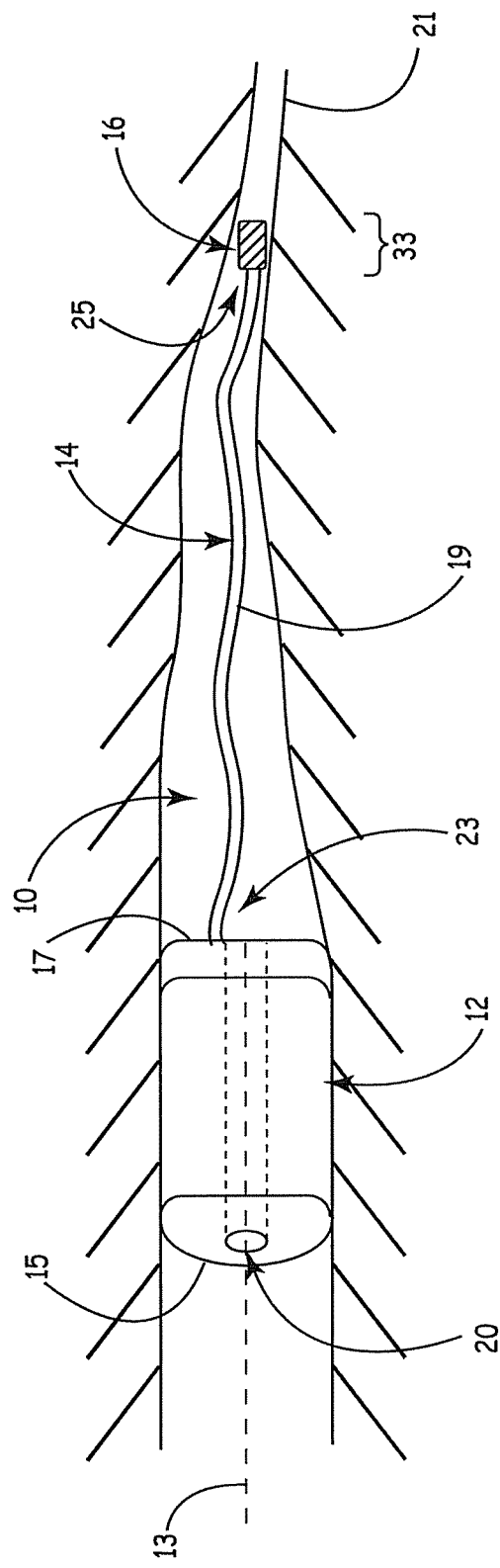
FIG. 2 is a illustration of an exemplary embodiment of an IVMD including a housing module for containing one or more circuitry components and a lead including an electrode for implant as shown in FIG. 1.

FIGS. 1-2 illustrate an exemplary intravascular medical device (IVMD) 10. The IVMD 10 is an implantable medical device that includes a hermetically sealed housing module 12 containing circuitry components to control, power, and operate the device 10. The housing module 12 is shaped and configured to reside entirely within the vasculature anatomy (e.g., of the heart, lungs, kidney, pancreas, etc.). Further, the IVMD 10 includes at least one lead 14 that incorporates at least one electrode 16.

The IVMD 10 may have any one or more functional capabilities including sensing, diagnostic, communications and therapy delivery. For example, as further described herein, the IVMD 10 may include cardiac sensing, pacing and defibrillation capabilities as well as the ability to communicate with an external device through telemetry.

As shown in FIGS. 1-2, the housing module 12 extends between a proximal end 15 and a distal end 17 (e.g., to contain one or more circuitry components) within a vessel 21. An opening 20 (e.g., a thru-hole) is defined through the elongated housing module 12 from the proximal end 15 to the distal end 17. In one embodiment, the housing module 12 is an elongated housing module that extends between proximal end 15 and distal end 17 along axis 13 (e.g., the opening 20 being centered on the axis 13; with the axis 13 defining the center of the housing module 12).

The at least one lead 14 of the IVMD 10 which incorporates the at least one electrode 16 extends between a proximal end 23 and a distal end 25 within the vessel 21. In one or more embodiments, the proximal end 23 of the lead 14 is coupled towards the distal end 17 of the elongated housing module 12. At least one electrode 16 is located in proximity to the distal end 25 of the lead 14.

The location of the at least one electrode 16 changes during implant of the IVMD 10 (e.g., into a vessel 21). In one or more embodiments, at least a portion of the at least one electrode 16 is in a stowed position within the opening 20 defined through the elongated housing module 12 during implant of elongated housing module 12 of the IVMD 10 (see, e.g., a stowed configuration of the IVMD 10 in FIG. 6 wherein at least a portion of the electrode 16 is shown to be positioned within the opening 20 prior to be deployed more distally in the vessel structure). Further, in one or more embodiments, the at least one electrode 16 is advanceable from the stowed position to a location distal of the distal end 17 of the elongated housing module 12 (see, e.g., an advanced configuration of the IVMD 10 in FIG. 5 wherein the electrode 16 is shown to be advanced from the opening 20 to a location distal of the elongated housing module 12).

Figure 3:
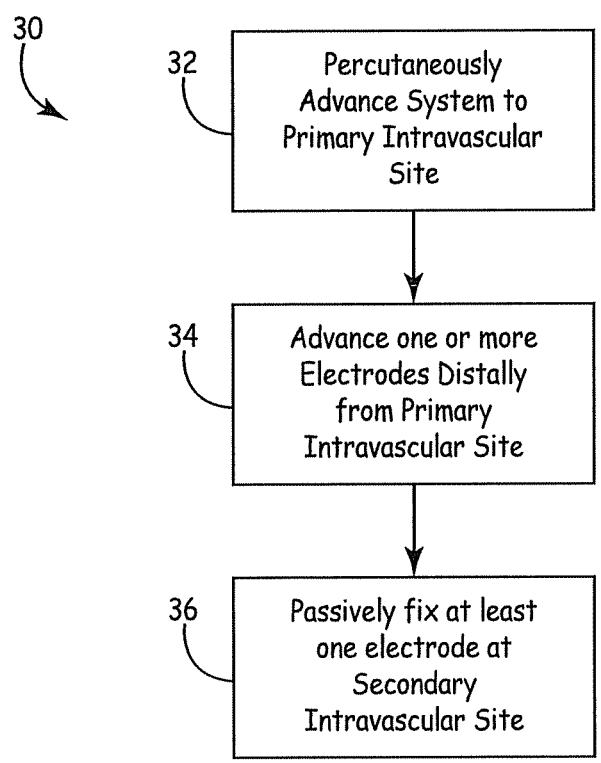
FIG. 3 is an exemplary embodiment of a flowchart describing a process for implanting an IVMD such as shown in FIG. 1-2.
Figure 4:
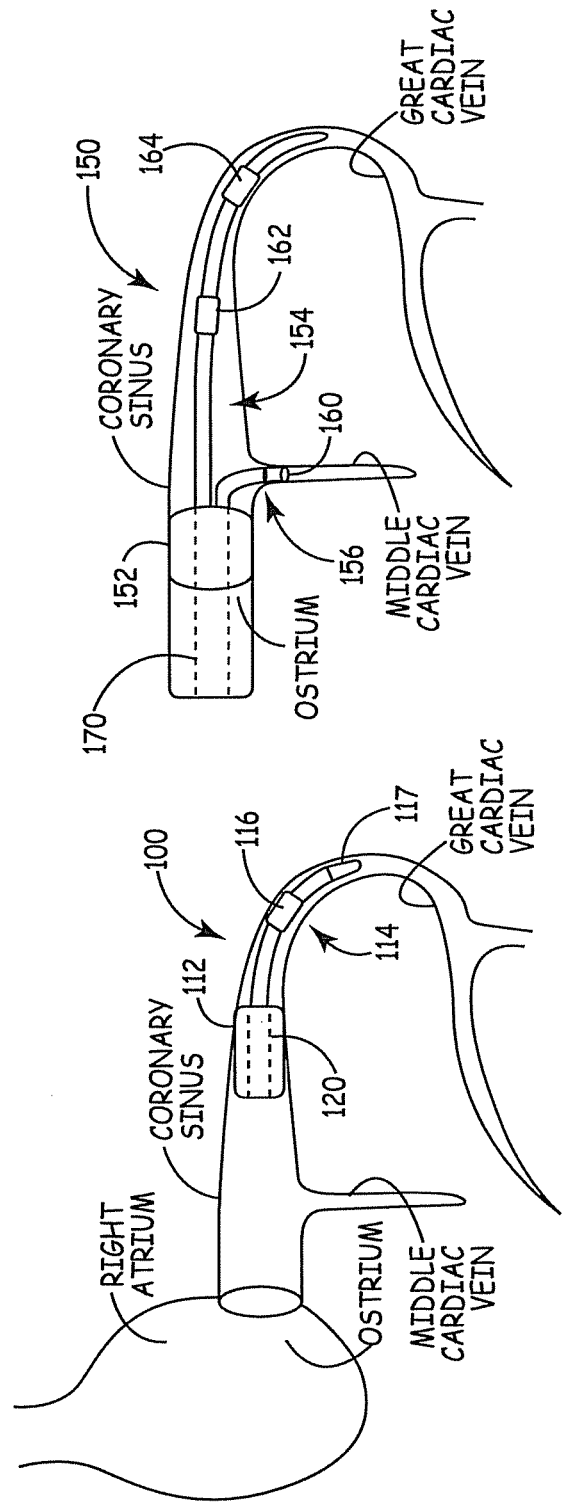
FIG. 4A illustrates an exemplary embodiment of an IVMD having a lead that includes multiple electrodes.
FIG. 4B illustrates an exemplary embodiment of an IVMD having multiple leads, each lead including at least one electrode.

FIG. 3 shows an exemplary embodiment of a flowchart describing a general implant method 30 for implanting an IVMD such as the IVMD 10 shown in FIGS. 1-2. For example, generally, the IVMD 10 with the at least one electrode 16 in a stowed position is percutaneously advanced to a primary intravascular site 31 (see FIG. 2) (block 32). Thereafter, the at least one electrode 16 is advanced from the stowed position and moved distally from the primary intravascular site (block 34) to a secondary intravascular site 33. In one or more embodiments of the method 30, the at least one electrode 16 may be passively fixated at the secondary intravascular site 33 (block 36).

In other words, in one or more embodiments, the IVMD is to be delivered percutaneously. For example, access to the venous system can be attained via the femoral vein, jugular vein, subclavian vein, or any other useful or similar vasculature. A dilator, or multiple dilators of increasing size, may be used to create an access site into the vein. Further, an introducer sheath may then be placed into the vein to facilitate continual access to the vein throughout the procedure.

In one or more embodiments, the IVMD 10 with the at least one electrode 16 in a stowed position may be delivered on a catheter that may enable the use of a guide wire and/or have steerable/articulating capabilities. The system (e.g., the IVMD 10 with the at least one electrode 16 in a stowed position) may be advanced to the right atrium from the inferior vena cava or the superior vena cava, depending on the access site. The system may then enter (e.g., be advanced to) the coronary sinus from the right atrium.

Once in the coronary sinus, the IVMD 10 with the at least one electrode 16 in a stowed position may be advanced distally as fax as possible (e.g., depending on size of the housing module of the IVMD 10 and size of the vessel). For example, an interference fit between an outer surface of the main body of the housing module 12 (e.g., a pacer housing module) and the vessel lumen wall of the coronary sinus may be created to fixate the housing module 12 of the IVMD 10 within the coronary sinus (e.g., passively fixate the housing module 12 within the vessel).

With the housing module 12 fixated in the vessel (e.g., at the primary intravascular site 31), the electrode 16 of the IVMD 10 may then be advanced further distal in the main trunk of the coronary sinus, or down one of the side branches of the coronary sinus. For example, the advancement of the electrode 16 may be facilitated by a push rod or similar structure that has adequate column strength to advance (e.g., push) the electrode 16 into the distal regions of the coronary veins. In one or more embodiments, the push rod may be incorporated into the delivery system or it may be a separate component that is introduced into the vein after the delivery system is removed. The electrode 16, for example, may have a center or side lumen that is compatible with a guide wire, which may help direct the electrode 16 to the target vessel (e.g., the secondary intravascular site 33). In one or more embodiments, the electrode 16 is advanced as distally as possible (e.g., depending on the size of the electrode 16 of IVMD 10 and size of the vessel). For example, an interference fit between an outer surface of the electrode 16 and the vessel lumen wall may be created to fixate the electrode 16 within the vessel (e.g., passively fixate the electrode 16 within the vessel).

Extending out the electrode 16 from the main body of housing module 12 of the IVMD 10 (e.g., advancing the electrode from the opening of a pacer housing module)

reveals the thru-hole 20 (e.g., opening) that passes through the housing module 12. As described herein with reference to FIGS. 7A-7B, the thru-hole may be centered along the same axis 13 as the main body of the housing module 12, or, as described herein with reference to FIGS. 8A-8B, the thru-hole may be off-center to allow for the internal electronic components and power supply of the IVMD (e.g., pacer) to be configured in a different layout. The thru-hole (e.g., opening 20) whether centered on or off-centered from the axis 13 of the housing module 12, allows blood flow to pass therethrough so that the coronary sinus is not fully obstructed and can still function adequately.

The lead 14 includes one or more lead wires 19 that connect the electrode 16 to the main body of the IVMD 10 (i.e., to the housing module 12) and is of adequate length to allow the electrode 16 to be placed at the target implant site (e.g., the secondary intravascular site 33). As further described herein, in one or more embodiments, to facilitate variable distances from the electrode 16 to the housing module 12 (e.g., main body of a pacer housing module), the lead 14 and other components of the IVMD may be of one or more multiple configurations. For example, the lead wire 19 may be in a set helical shape so that it can expand and contract to the needed distance. The lead wire 19 may also be housed within the housing module 12 (e.g., the main body of a pacer housing module) and be extendable out from a contained section thereof to a needed length.

The implant process was described with reference to the coronary sinus and its branches. However, such processes may be carried out with respect to or within any vascular structure.

FIG. 4A illustrates an exemplary embodiment of an IVMD 100 having a lead 114 advanced into the coronary sinus from an opening 120 defined in elongated housing module 112. The lead 114 includes multiple electrodes 116, 117; electrode 117 being more distal on lead 114 than electrode 116. For example, both of such electrodes 116, 117 (or at least portions thereof) may have been positioned within opening 120 in a stowed configuration when the elongated housing module 112 was implanted to the primary intravascular site. Thereafter, lead 114 may have been advanced distally from the housing module 112 within the coronary sinus until at least electrode 117 was passively fixated in the vessel (e.g., interference fit). In one or more embodiments, both electrodes 116, 117 may be passively fixated within the vessel. For example, electrode 116 may be relatively larger in diameter than electrode 117.

Still further, in one or more embodiments, electrode 116 may include a lumen in which electrode 117 may be stowed, partially or entirely. For example, during implant, electrode 116 including such a stowed electrode 117 (e.g., within a lumen thereof) may be advanced forward into the vessel using a pushing tool until it is passively fixated within the vessel. Thereafter, electrode 117 stowed within the lumen of electrode 116 may be advanced forward (i.e., more distally) into the vessel using a pushing tool until it is passively fixated within the vessel.

FIG. 4B illustrates an exemplary embodiment of an IVMD 150 having multiple leads 154, 156 advanced from one or more openings 170 defined in elongated housing module 152. The lead 154 includes multiple electrodes 162, 164, in a manner such as described with reference to lead 114 of FIG. 4A. The lead 156 includes electrode 160 at the distal end thereof. In one or more embodiments, for example, all of such electrodes 162, 164, and 160 (or at least portions thereof) may have been positioned within opening 170 in a stowed configuration when the elongated housing module 152 was implanted to the primary intravascular site. Thereafter, lead 154 may have been advanced distally from the housing module 152 within the coronary sinus until at least electrode 164 was passively fixated in the vessel (e.g., interference fit). In one or more embodiments, both electrodes 162, 164 may be passively fixated within the vessel. For example, electrode 162 may be relatively larger in diameter than electrode 164. Further, lead 156 may have been advanced distally from the housing module 152 within the middle cardiac vein until electrode 160 was passively fixated in the vessel (e.g., interference fit).

Although the housing module 152 is shown as including only a single opening 170, multiple openings may be present for stowing the different leads 154, 156. Each of such leads 154, 156 may then be individually advanced distally from the housing module 152 and passively fixated in the respective vessels (e.g., interference fit). Such additional openings may be suitable for blood flow therethrough or may only be used to receive tools that may be used to advance the electrode to its respective location (e.g., an advancing push rod and/or guidewire).

Various tools are described herein for implanting the IVMDs (e.g., advancing one or more components thereof within one or more vessels). However, one skilled in the art will recognize that various delivery tools may be used to position such components at one or more sites within the one or more vessels. For example, any number of types of catheters, stylets, guide wires, or other tools may be used to implant such IVMD components and the present disclosure is not limited to those described herein.

Figure 5:
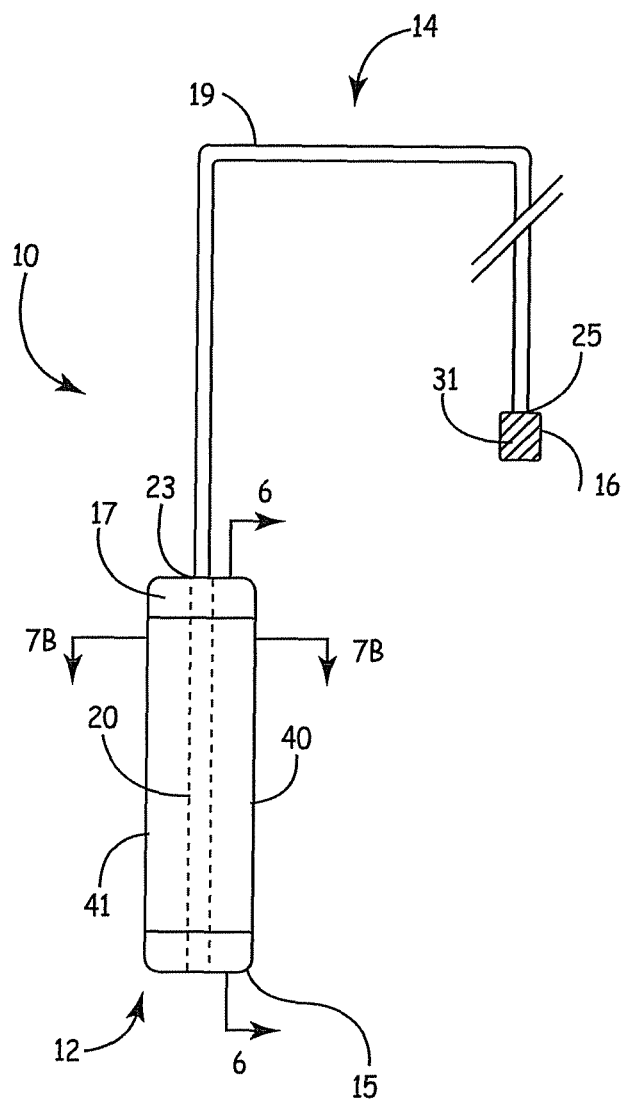
FIG. 5 is a plan view of an exemplary embodiment of an IVMD having a lead coupled to a distal end of a housing module for containing one or more circuitry components; the electrode of the IVMD being in an advanced position.
Figure 6:
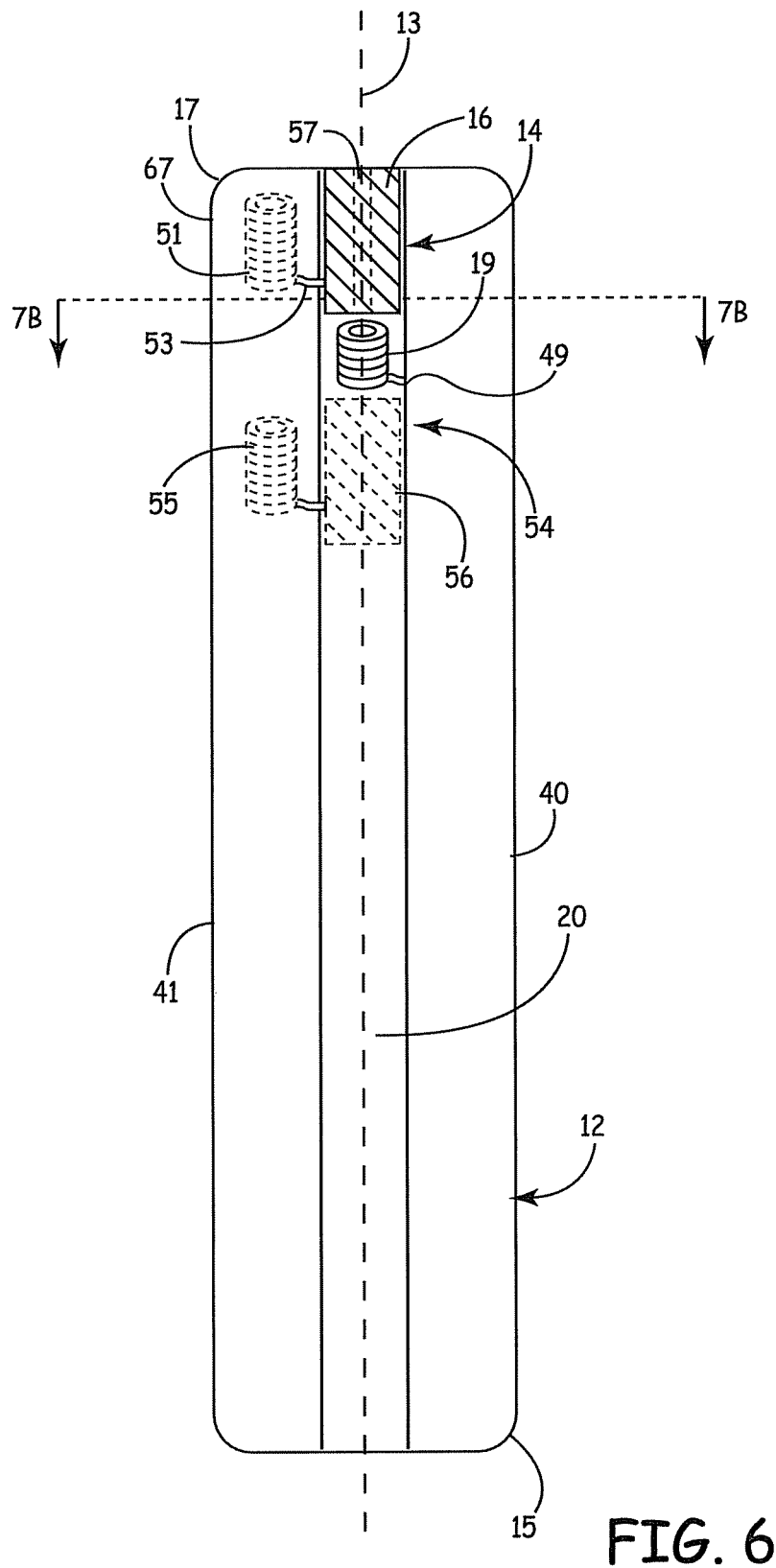
FIG. 6 is a sectional view of the housing module of the IVMD of FIG. 5 taken along line 6-6 of FIG. 7A; the electrode of the IVMD being in a stowed configuration.

FIG. 5 is a plan view of an exemplary embodiment of IVMD 10 having lead 14 coupled towards distal end 17 of housing module 12 for containing one or more circuitry components. In FIG. 5, the electrode 16 of the IVMD is in an advanced position. FIG. 6 is a sectional view of the housing module 12 of the IVMD 10 of FIG. 5 taken along line 6-6 of FIG. 7A. In FIG. 6, the electrode 16 of the IVMD 10 is in a stowed configuration (e.g., at least partially within opening 20 of the elongated housing module). Still further, FIG. 7A illustrates an end view of the IVMD 10 of FIG. 5 with the electrode 16 of the IVMD 10 being in a stowed configuration as shown in FIG. 6, and FIG. 7B shows a sectional view of the IVMD 10 of FIG. 5 taken along line 7B-7B thereof but with the electrode 16 being in a stowed configuration as shown in FIG. 6 (see same section line 7B-7B in FIG. 6).

As shown in FIGS. 5-7, the elongated housing module 12 includes a main body portion 40 that extends between proximal end 15 and distal end 17 thereof along axis 13. The opening 20 is defined through the elongated housing module 12 and is centered along the axis 13. The elongated housing module 12 may be formed of one or more components or portions. For example, the ends 15, 17 terminating the main body portion 40 may be formed for ease of delivery or advancement/withdrawal of the housing module 12 (e.g., such ends may be chamfered, curved, or otherwise provide surfaces beneficial for moving of the housing 12 through vessels).

Figure 7A:
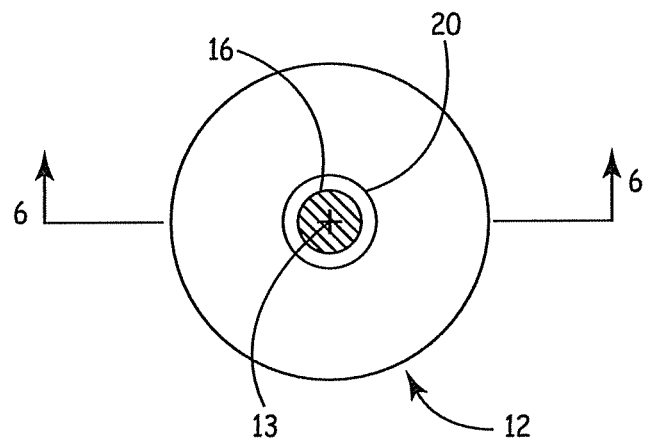
FIG. 7A illustrates an end view of the IVMD of FIG. 5 with the electrode of the IVMD being in a stowed configuration as shown in FIG. 6.
Figure 7B:
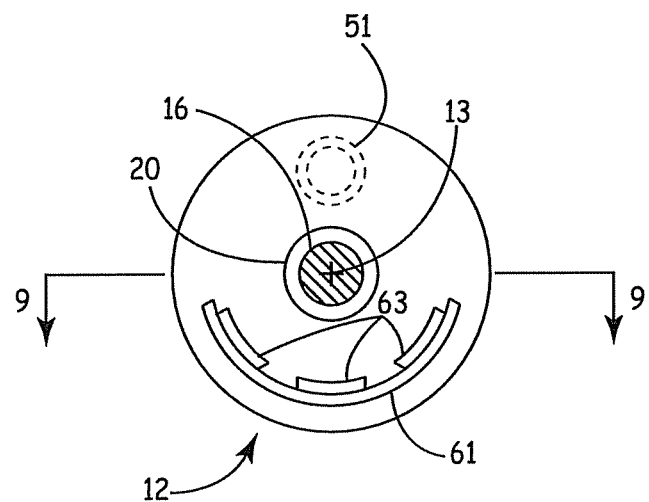
FIG. 7B shows a sectional view of the IVMD of FIG. 5 taken along line 7B-7B thereof but with the electrode being in a stowed configuration as shown in FIG. 6 (see same section line 7B-7B in FIG. 6).
Figure 8A:
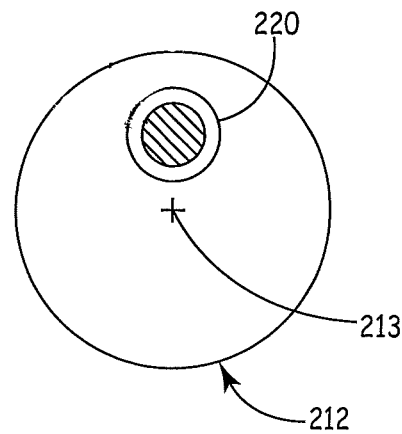
FIGS. 8A-8B illustrate another embodiment of an IVMD in the same manner as shown in FIGS. 7A-7B but with the opening defined through the housing module being offset from the center axis, and an alternate circuitry configuration within the housing module.
Figure 8B:
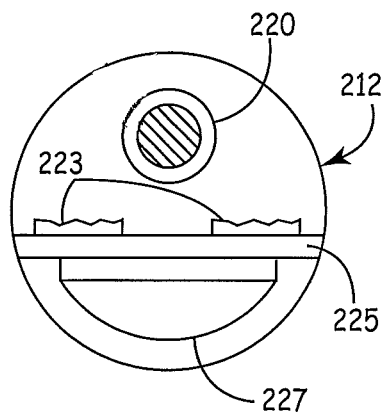

Although the opening 20 is shown in FIGS. 5-7 as being centered along the axis 13 (e.g., the center axis of the elongated housing module 12), the opening may be defined through the elongated housing module offset from the axis. For example, FIGS. 8A-8B illustrate another embodiment of an IVMD including a housing module 212 that extends along a center axis 213 in the same manner as shown in FIGS. 7A-7B but with the opening 220 defined through the housing module 212 being offset from the center axis 213. In such a manner, alternate circuitry configurations may be possible within the housing module 212 due to the presence of more volume for such circuitry on one side of the elongated housing module 212 than when the opening is centered (e.g., such as shown in FIGS. 5-7).

As shown in FIG. 5, the lead 14 extends from proximal end 23 to distal end 25. The electrode 16 is located at the distal end 25 of the lead 14 and is configured to be passively fixated within vascular structure such that at least two opposing surface regions are lodged within the vascular structure. In other words, if the electrode 16 is circular in shape, than an interference fit between an outer surface 31 of the electrode 16 with the inner surface of the vessel provides for the passive fixation of the electrode 16 within the vessel (e.g., more than two opposing surface regions provide such an interference fit).

For example, in one or more embodiments, the outer surface 31 configured for contact with the vessel wall of vascular structure (e.g., in an interference fit) may have an outer diameter greater than 0.1 mm, greater than 0.2 mm, or greater than 0.5 mm. Further, in one or more embodiments, the outer diameter may be less than 1 mm, less 2 mm, or less than 5 mm. At least in one embodiment, the outer diameter of the electrode is in the range of 0.1 mm to 5 mm.

Figure 10:
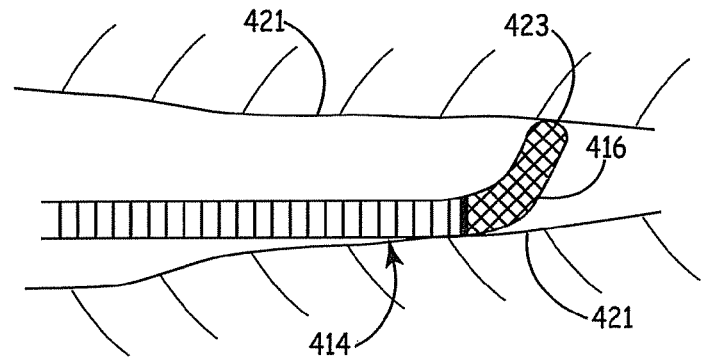
FIG. 10 illustrates a plan view of an exemplary embodiment of a passively fixated electrode configuration that may be used in the IVMD.

As shown in FIGS. 10-12, various electrode structures may be use to provide for passive fixation of one or more electrodes as described herein (e.g., a ring electrode towards the distal end of the lead passively fixed within the vessel). For example, in each of such embodiments at least two opposing surface regions lodge the electrode within the vessel in which it is fixated.

For example, as shown in FIG. 10, a tip electrode 416 at the distal end of lead 414 may be passively fixated in vessel 421. The electrode 416 is provided in a curved configuration such that when the electrode 416 is advanced into the vessel 414 the surface region 423 towards the tip of the lead 414 and a surface region 421 proximal thereof (e.g., part of the electrode or not) provides for lodging the electrode 416 within the vessel 421.

Figures 11A, 11B:
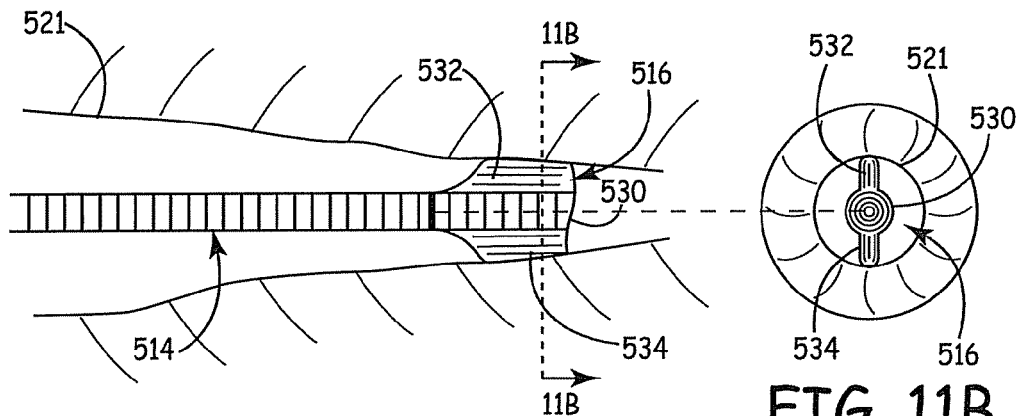
FIGS. 11A-11B illustrates a plan view and a section view of another exemplary embodiment of a passively fixated electrode configuration that may be used in the IVMD.

Further, for example, as shown in FIGS. 11A-11B, electrode 516 at the distal end of lead 514 is passively fixated in vessel 521. The electrode 516 is provided in a winged configuration including a central region 530 and opposing wing regions 532, 534. In such a configuration, when the electrode 516 is advanced into the vessel 514, the surface regions of the opposing wing regions 532, 534 come into contact with portions of the vessel walls and provide for lodging the electrode 516 within the vessel 521.

Figures 12A, 12B:
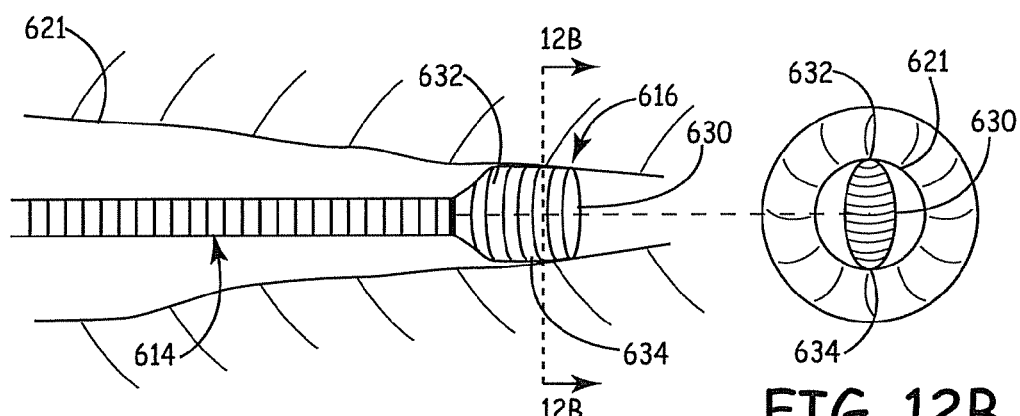
FIGS. 12A-12B illustrates a plan view and a section view of yet another exemplary embodiment of a passively fixated electrode configuration that may be used in the IVMD.

Further, for example, as shown in FIGS. 12A-12B, electrode 616 at the distal end of lead 614 is passively fixated in vessel 621. The electrode 616 is provided in an oblong configuration including a central surface region 630 (e.g., not in contact with the vessel wall when fixated) flowing to contact regions 632, 634 (e.g., which are in contact with the vessel wall when the electrode 616 is fixated in vessel 621). In such a configuration, when the electrode 616 is advanced into the vessel 614, the opposing surface regions 632, 634 of the oblong configuration come into contact with portions of the vessel walls and provide for lodging the electrode 616 within the vessel 621.

Although the electrodes thus far described for use with the IVMD 10 are passively fixated alone and without any fixation apparatus, other electrodes may be used that include or are associated with one or more different features that actively fixate the electrode to the vessel. For example, the electrode may be attached to a vessel using a fixation device (e.g., anchoring structures, expandable scaffold frames, tissue penetrating anchors, etc.).

The lead 14 and the relative position of one or more electrodes may be determined based upon the type of therapies, sensing and diagnostics provided and the implant location of the IVMD 10. The lead 14 may have other functions instead of or in addition to electrical stimulation or sensing. For example, a number of non-electrical parameters (e.g., pressure, temperature, velocity, chemical presence/concentration, etc.) may be sensed by providing an appropriate sensor. The lead 14 may have a delivery device to deliver drugs, genetic material, or biologics from a reservoir in the housing module 12 (e.g., a needle for delivery into tissue; a disbursing tip (e.g., a porous surface for release into a fluid supply or against a larger surface area); or a variety of other delivery mechanisms.

As further shown in FIGS. 6-7, the electrode 16 is entirely located within the opening 20 at the distal end 17 of the elongated housing module 12 in the stowed position (e.g., stowed configuration used during implant of the elongated housing 12). This is unlike the position of the electrode 16 as shown in FIG. 5 in the advanced configuration (e.g., non-stowed position) where the electrode 16 has been advanced or moved from within the opening 20. Further, the electrode 16, for example, may have a center lumen 57 (or any other positioned lumen, such as on the side) that is compatible with a guide wire, and which may help direct the electrode 16 to the target vessel (e.g., the secondary intravascular site 33) as described herein.

As shown in FIG. 6, the lead 14 in the stowed configuration includes a lead wire 19 (e.g., a coiled lead wire allowing for advancement of the electrode to the desired placement within the vessel; the lead wire being advanced to a desire length) coupling the electrode 16 to the one or more circuitry components contained within the elongated housing module 12. For example, at least a portion of the lead wire 19 is in a stowed position within the opening 20 defined through the elongated housing module 12 during implant of the implantable medical device 10. In one or more embodiments, the proximal end 23 of the lead wire 19 is connected to the one or more circuitry components 63 as shown in FIG. 7B (e.g., pacing circuitry) contained within the elongated housing module 12 via a sealed feedthrough 49. Any number of different connection techniques may be used to couple the lead to the circuitry (e.g., pin connections, feedthroughs, etc.). At least a portion of the lead wire 19 is advanceable with the electrode 16 from the stowed position in the opening 20 to a positioned distal from the housing module 12.

In one or more other embodiments, the lead wire may be a lead wire 51 (coiled as shown in dashed lines) coupling the electrode 16 to the one or more circuitry components 63 contained within the elongated housing module 12. For example, at least a portion of the lead wire 51 may be in a stowed position within a containment section 67 in the elongated housing module 12 (e.g., at the distal end 17 thereof) during implant of the housing module 12 of the implantable medical device 10, as opposed to being within the opening 20. The lead wire 51 may be advanceable with the electrode 16 from the stowed position through a feed through 53 (e.g., sealed if needed) that allows the lead wire 51 to be advanced therethrough.

The IVMDs described herein allow for the use of short leads. In one or more exemplary embodiments, the length of such leads (i.e., the distance from the distal end 17 of elongated housing module 12 to the distal end 25 of the lead 14) may be less than 5 cm, less than 15 cm, less than 25 cm, or less than 100 cm.

As described herein, and as shown in at least FIG. 6, the IVMD 10 may include two or more leads (e.g., leads 14, 54), wherein each lead 14, 54 includes at least one electrode 16, 56, respectively, located in proximity to the distal end of the lead 14, 54. In FIG. 6, each electrode 16, 56 of each lead 14, 54 is in a stowed position within the opening 20 defined through the elongated housing module 12 during implant of the IVMD 10. The lead wires thereof (e.g., wires 19, 51, 55) are also shown in multiple possible configurations as described herein (e.g., in the opening 20, in a containment section within the housing module 12, etc.).

As shown in FIG. 6, the elongated housing module 12 of the IVMD 10 may also be configured to be passively fixated within vascular structure (e.g., with the electrode or electrodes in stowed positions). For example, the housing module 12 may be configured to be passively fixated within vascular structure such that at least two opposing surface regions thereof are lodged within the vascular structure. In other words, if the housing module 12 has a circular cross-section shape, than an interference fit between an outer surface 41 thereof with the inner surface of the vessel provides for the passive fixation of the housing module 12 within the vessel (e.g., more than two opposing surface regions provide such an interference fit).

For example, in one or more embodiments, the outer surface 41 configured for contact with the vessel wall of vascular structure (e.g., in an interference fit) may have an outer diameter greater than 4 mm, greater than 8 mm, or greater than 12 mm. Further, in one or more embodiments, the outer diameter may be less than 20 mm, less than 15 mm, or less than 10 mm. At least in one embodiment, the outer diameter of the housing module is in the range of 4 mm to 15 mm.

Further, the housing module may be passively fixated without use of any fixation apparatus (e.g., which actively fix components). For example, the housing module may have a cylindrical structure or a structure like that of the electrodes shown in FIGS. 10-12 and/or include one or more surface finishes to facilitate passive fixation. However, in one or more embodiments, housing module may be associated with one or more different features that actively fixate the housing module with the vessel. For example, the housing module may be associated with various fixation devices to attach the housing module to a vessel (e.g., anchoring structures, suture structure, expandable scaffold frames, tissue penetrating anchors, etc.).

As shown in FIG. 7B, circuitry components 63 may be mounted on a board 61 within the housing module 12 (e.g., a flexible circuit board). Such circuitry components 63 may include any components required for operation of the IVMD, and the present disclosure is not restricted to only those components listed herein or the functionality listed herein that may be carried out thereby.

Figure 9:
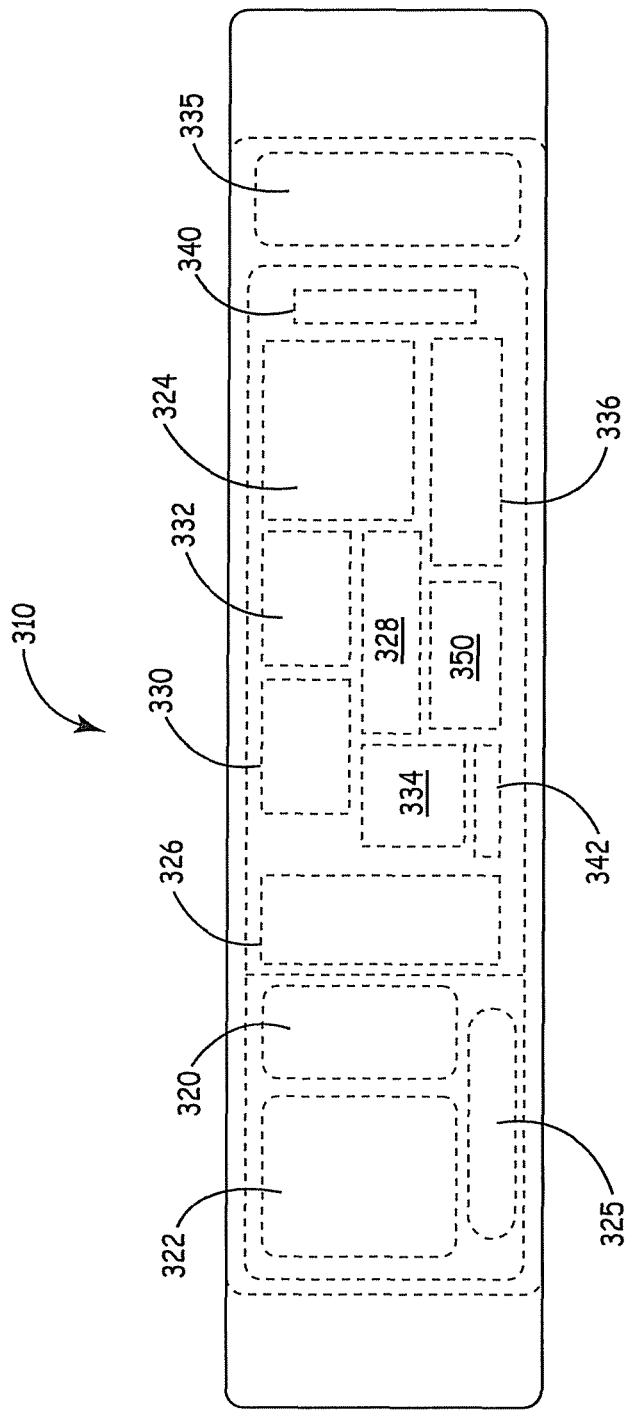
FIG. 9 illustrates an exemplary embodiment of a sectional view of the IVMD of FIG. 5 taken along line 9-9 thereof (see same section line 9-9 in FIG. 6) showing selected circuitry components of the IVMD.

For example, in one or more embodiments, the components 63 may include components 310 such as shown in FIG. 9. For example, the components may include a power source 320, such as a battery. One or more capacitors 322 may be provided that allow charge to be accumulated for rapid discharge to deliver a defibrillation or cardioversion pulse. A pulse generator 326 may be coupled to the power source 320 and provide electrical stimuli for cardiac pacing.

Still further, a microprocessor 324, memory 336 (flash, EEPROM, ROM, RAM, DRAM, hard disk, etc.), analog to digital converter 330, analog signal processor 328, and digital signal processor (DSP) 332 may be positioned within the housing module. An externally actuated switch 342 may be provided and may take the form of a reed switch that is closed by a magnet. Such a switch 342 may be used to initiate a telemetry session with IVMD 10. Alternatively, communication may be initiated directly by an RF signal or other appropriate transmission medium. A telemetry module 334 may provide the ability to transmit and receive data. A reservoir 335 may be optionally included. The reservoir may provide a supply of a deliverable drug (e.g., insulin), genetic material, or biologic. The IVMD 10 may provide for the release of the material on a given schedule or based upon sensed need. Some materials, such as insulin, may be dispersed as needed but are predictably used; that is, the likelihood of delivery over a given time period is high. Other material may be delivered on an acute basis. For example, a dose of a blood thinner, coagulant, anti-coagulant, or adrenaline is provided and released when necessitated.

An accelerometer 340 may be utilized to provide an indication of patient activity for a rate response function and/or a relative position indicator; that is, physical position of the patient (e.g., prone). Finally, a sensor array 350 is illustrated. The sensor array 350 may sense any number of parameters such as temperature, pressure, velocity or other fluid flow characteristics, impedance, motion or size (e.g., ultrasound for wall motion and/or chamber size), oxygenation, glucose, or the level of any sensed chemical substance. It should be appreciated that while illustrated as contained within the housing, the sensor array 350 may have appropriate external portions not shown. For example, if used as a pressure sensor, a transducing membrane may form a part of the housing module or part of a lead coupled with the housing module, either physically or through telemetric connection (e.g., a body bus). Likewise, any additional component(s) for sensor array 350 may be included in this manner. Cardiac data (e.g., electrogram (EGM)) may be sensed via one or more leads. In addition, the housing module may include one or more electrodes incorporated into the structure of the housing module (e.g. an active "module" or "capsule").

Still further, the power source 320 may be a single use battery. Alternatively, the battery may be rechargeable. As such, an optional recharging module 325 may be used. The recharging module 325 may receive power from an external source, such as directed RF energy, which is converted and used to recharge the battery 320. The RF energy may be collected via one or more antenna as discussed below, by using the housing module as an antenna, or by incorporating a receiver into the housing module. Alternatively, or in addition, the recharging module 325 may use other mechanisms to generate power. In other words, various techniques are available to recharge the battery and are considered to be within the scope of the present disclosure.

The module 325 has been described in conjunction with a traditional rechargeable battery 320 as a mechanism to recharge that battery. It should be appreciated that to conserve space, the traditional battery 320 may be eliminated or greatly reduced in size (due to a decrease in reliance upon the battery). That is, various mechanisms may be used to generate electrical energy from sources around the IVMD 10 to directly power the IVMD 10, without first storing that energy in a battery. In one embodiment, for example, providing power directly may be utilized when the IVMD has low or minimal power consumption requirements (e.g., periodic sensing). Thus, power may be generated for internal operations and when communication is desired, external power may be provided for e.g., telemetry functions, through inductive coupling or RF power transmission. Of course, the IVMD 10 may be completely dependant upon such power conversion for all of its functionality. Finally, as indicated, a smaller battery or capacitor may be provided to collect some amount of energy prior to use; either to mitigate against fluctuation in the source or to provide an even power supply to mitigate against power fluctuations; that is, to provide a relatively stable DC source.

Further, an antenna may extend from the housing module 12 and may be contained within or affixed to an outer portion of the lead. The antenna may be used for communication and/or as an RF collector to receive power to recharge the power source 320. Furthermore, multiple antennas may be provided to facilitate different types of communication; to have a different antenna for transmission versus reception; to provide a separate power collector, to provide low and high power communication formats, to provide redundancy or for any number of reasons. One or more antennas may also be included in the lead 14.

As described herein, the IVMD 10 may include multiple leads with each of these leads attached or coupled with the housing module 12. Due to the size and implant location of IVMD 10, particular configurations of the housing module 12 may make attachment of more than two leads difficult. In such a case, in one or more embodiments, multiple IVMDs 10 may be used. The separate IVMDs 10 may be in wireless communication so that their activities are synchronized. For example, one IVMD may provide atrial pacing and another may provide ventricular pacing. The multiple IVMDs 10 may be completely independent and simply communicate to one another to synchronize timing. Alternatively, one IVMD 10 may act to control the functions of one or more other IVMDs. The multiple IVMDs 10 may be implanted through the same entry point and reside in the same anatomical location or proximate one another. Alternatively, the multiple IVMDs may be implanted from different locations and reside remotely from one another, while retaining wireless communication.

As shown in FIG. 8B, where the opening 220 is offset from the center axis 213, circuitry components 223 (e.g., processors, pacing circuits, etc.) may be mounted one side of a circuit board 225 with other components 227 (e.g., power or battery components) may be mounted on the other side of the board 225 within the housing module 212. Such circuitry components 223 and their configuration within the housing module 212 may include any components and configuration required for operation of the IVMD, and the present disclosure is not restricted to only those components or configurations listed herein or the functionality listed herein that may be carried out thereby.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed is:

1. An intravascular implantable medical device comprising:
    one or more circuitry components comprising at least one of processing circuitry and a power source;
    an elongated housing module extending between a proximal end and a distal end to contain the one or more circuitry components and configured to reside entirely within a vascular structure, wherein an opening is defined through the elongated housing module from the proximal end to the distal end, wherein the intravascular implantable medical device is configured to be delivered to a position within the vascular structure using a delivery apparatus removable from the vascular structure after delivery of the intravascular implantable medical device, and further wherein the elongated housing module of the intravascular implantable medical device is configured to be fixated at the position within the vascular structure, the elongated housing module comprising an outer surface configured for contact with a vessel wall of the vascular structure; and
    a lead extending between a proximal end and a distal end, wherein the proximal end of the lead is coupled towards the distal end of the elongated housing module, wherein the lead comprises at least one electrode located in proximity to the distal end of the lead, wherein at least a portion of the at least one electrode is in a stowed position within the opening defined through the elongated housing module during implant of the implantable medical device, and further wherein the at least one electrode is advanceable from the stowed position to a location distal of the distal end of the elongated housing module.

2. The device of claim 1, wherein the elongated housing module extends between the proximal end and the distal end along an axis, wherein the opening defined through the elongated housing module is centered along the axis.

3. The device of claim 1, wherein the elongated housing module extends between the proximal end and the distal end along an axis, wherein the opening defined through the elongated housing module is offset from the axis.

4. The device of claim 1, wherein the at least one electrode comprises an electrode at the distal end of the lead, and further wherein the electrode at the distal end of the lead is configured to be passively fixated within a vascular structure, at least two opposing surfaces of the at least one electrode being adapted to be lodged within the vascular structure.

5. The device of claim 1, wherein the at least one electrode comprises an outer surface configured for contact with a vessel wall of a vascular structure and comprises an outer diameter in the range of 0.1 mm to 5 mm.

6. The device of claim 1, wherein the at least one electrode is entirely located within the opening defined through the elongated housing module in the stowed position.

7. The device of claim 1, wherein the device comprises two or more leads, wherein each lead comprises at least one electrode located in proximity to the distal end of the lead, wherein at least a portion of the at least one electrode of each lead is in a stowed position within the opening defined through the elongated housing module during implant of the implantable medical device.

8. The device of claim 1, wherein the elongated housing module is configured to be passively fixated within the vascular structure.

9. The device of claim 1, wherein the outer surface configured for contact with a vessel wall of the vascular structure comprises an outer diameter in the range of 4 mm to 15 mm.

10. The device of claim 1, wherein the lead comprises a lead wire coupling the at least one electrode to the one or more circuitry components contained within the elongated housing module, wherein at least a portion of the lead wire is in a stowed position within the opening defined through the elongated housing module during implant of the implantable medical device, and further wherein the lead wire is advanceable with the at least one electrode from the stowed position.

11. The device of claim 1, wherein the lead comprises a lead wire coupling the at least one electrode to the one or more circuitry components contained within the elongated housing module, wherein at least a portion of the lead wire is in a stowed position within a containment section in the elongated housing module during implant of the implantable medical device, and further wherein the lead wire is advanceable with the at least one electrode from the stowed position.

12. A method comprising:
    advancing an implantable medical device to a primary intravascular site of a vascular structure using a removable delivery apparatus, wherein the implantable medical device comprises:
        one or more circuitry components comprising at least one of processing circuitry and a power source;
        an elongated housing module extending between a proximal end and a distal end to contain the one or more circuitry components and configured to reside entirely within a vascular structure at the primary intravascular site, wherein an opening is defined through the elongated housing module from the proximal end to the distal end, and
        a lead extending between a proximal end and a distal end, wherein the proximal end of the lead is coupled towards the distal end of the elongated housing module, wherein the lead comprises at least one electrode located in proximity to the distal end of the lead, wherein at least a portion of the at least one electrode is in a stowed position within the opening defined through the elongated housing module as the implantable medical device is advanced to the primary intravascular site;
    fixating the elongated housing module at the primary intravascular site;
    advancing the at least one electrode from the stowed position to another intravascular site distal of the distal end of the elongated housing module; and
    removing the delivery apparatus from the vascular structure.

13. The method of claim 12, wherein the elongated housing module extends between the proximal end and the distal end along an axis, wherein the opening defined through the elongated housing module is centered along the axis or is offset from the axis.

14. The method of claim 12, wherein the at least one electrode comprises an electrode at the distal end of the lead, and further wherein the method comprises passively fixating the electrode at the distal end of the lead within a vascular structure at the another intravascular site.

15. The method of claim 14, wherein passively fixating the electrode at the distal end of the lead within the vascular structure comprises lodging two opposing surface regions of the electrode within the vascular structure.

16. The method of claim 12, wherein the at least one electrode comprises an outer surface configured for contact with a vessel wall of a vascular structure and comprises an outer diameter in the range of 0.1 mm to 5 mm, and further wherein the method comprises passively fixating the at least one electrode within the vascular structure using an interference fit between the outer surface and the vessel wall.

17. The method of claim 12, wherein the implantable medical device comprises two or more leads, wherein each lead comprises at least one electrode located in proximity to the distal end of the lead, wherein at least a portion of the at least one electrode of each lead is in a stowed position within the opening defined through the elongated housing module, and further wherein the method comprises advancing the at least one electrode of each lead from the stowed position to separate intravascular sites distal of the distal end of the elongated housing module.

18. The method of claim 12, wherein the method further comprises passively fixating the elongated housing module within the vascular structure at the primary intravascular site.

19. The method of claim 12, wherein the outer surface configured for contact with a vessel wall of the vascular structure at the primary intravascular site comprises an outer diameter in the range of 4 mm to 15 mm, and further wherein the method comprises passively fixating the elongated housing module within the vascular structure at the primary intravascular site using an interference fit between the outer surface and the vessel wall.

20. The method of claim 12, wherein the lead comprises a lead wire coupling the at least one electrode to the one or more circuitry components contained within the elongated housing module, wherein at least a portion of the lead wire is in a stowed position within the opening defined through the elongated housing module during implant of the implantable medical device, and further wherein the method comprises advancing the lead wire with the at least one electrode from the stowed position to the intravascular site distal of the distal end of the elongated housing module.

21. The method of claim 12, wherein the lead comprises a lead wire coupling the at least one electrode to the one or more circuitry components contained within the elongated housing module, wherein at least a portion of the lead wire is in a stowed position within a containment section in the elongated housing module during implant of the implantable medical device, and further wherein the method comprises advancing the lead wire with the at least one electrode from the stowed position to the intravascular site distal of the distal end of the elongated housing module.

* * * * *